US012582291B2

(12) United States Patent
Komoro et al.

(10) Patent No.: US 12,582,291 B2
(45) Date of Patent: Mar. 24, 2026

(54) ENDOSCOPE AND ENDOSCOPE ILLUMINATION SUBSTRATE

(71) Applicant: HOYA CORPORATION, Tokyo (JP)

(72) Inventors: Atsushi Komoro, Tokyo (JP); Toshiki Watanabe, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 404 days.

(21) Appl. No.: 17/772,354

(22) PCT Filed: Nov. 2, 2020

(86) PCT No.: PCT/JP2020/041020
§ 371 (c)(1),
(2) Date: Apr. 27, 2022

(87) PCT Pub. No.: WO2021/090796
PCT Pub. Date: May 14, 2021

(65) Prior Publication Data
US 2022/0400933 A1 Dec. 22, 2022

(30) Foreign Application Priority Data
Nov. 6, 2019 (JP) ................................. 2019-201667

(51) Int. Cl.
*A61B 1/00* (2006.01)
*A61B 1/005* (2006.01)
*A61B 1/06* (2006.01)

(52) U.S. Cl.
CPC .......... *A61B 1/00071* (2013.01); *A61B 1/005* (2013.01); *A61B 1/06* (2013.01); *A61B 1/0676* (2013.01); *A61B 1/0684* (2013.01)

(58) Field of Classification Search
CPC ....... A61B 1/00071; A61B 1/005; A61B 1/06; A61B 1/0676
See application file for complete search history.

(56) References Cited

U.S. PATENT DOCUMENTS 8,685,005 B2 * 4/2014 Dahm .................. A61N 5/0601
606/2
2002/0188177 A1 * 12/2002 Miyanaga ............ A61B 1/0676
600/179
(Continued)

FOREIGN PATENT DOCUMENTS

JP H07327926 A * 12/1995
JP 11-253398 9/1999
(Continued)

OTHER PUBLICATIONS

JP201667378A English translation (Year: 2016).*
(Continued)

*Primary Examiner* — Michael J Carey
*Assistant Examiner* — Megan Elizabeth Monahan
(74) *Attorney, Agent, or Firm* — Greenblum & Bernstein, P.L.C.

(57) ABSTRACT

An endoscope or the like that prevents crosstalk between multiple light-emitting parts is provided. An endoscope includes: an observation window that is disposed at a distal end of an insertion part; a plurality of first light-emitting parts that are disposed around the observation window; a second light-emitting part that is disposed between the first light-emitting parts and emits light at a bandwidth different from a bandwidth of light emitted by the first light-emitting parts; and a light-shielding body that is disposed between one of the first light-emitting parts and the second light-emitting part.

14 Claims, 15 Drawing Sheets

(56)                References Cited

U.S. PATENT DOCUMENTS

| | | | |
|---|---|---|---|
| 2004/0225222 A1* | 11/2004 | Zeng ......................... | G01J 3/32 |
| | | | 600/476 |
| 2005/0124858 A1 | 6/2005 | Matsuzawa et al. | |
| 2009/0018398 A1 | 1/2009 | Segawa et al. | |
| 2010/0145415 A1 | 6/2010 | Dahm et al. | |

FOREIGN PATENT DOCUMENTS

| | | | | | |
|---|---|---|---|---|---|
| JP | 2005-74034 | 3/2005 | | | |
| JP | 2007-82820 | 4/2007 | | | |
| JP | 2007-173397 | 7/2007 | | | |
| JP | C2012-74417 | 4/2012 | | | |
| JP | 2014-2300 | 1/2014 | | | |
| JP | a 2015-53524 | 3/2015 | | | |
| JP | b 2015-185760 | 10/2015 | | | |
| JP | 2016-67378 | 5/2016 | | | |
| JP | 201667378 A * | 5/2016 | .............. | A61B 1/00 |
| JP | 2016067378 * | 5/2016 | .............. | A61B 1/00 |

| | | | | |
|---|---|---|---|---|
| JP | 2016067378 A | * | 5/2016 | |
| WO | 2007/125918 | | 11/2007 | |

OTHER PUBLICATIONS

JP2016067378 English Translation (Year: 2016).*
JPH07327926A English Translation (Year: 1995).*
Office Action issued in Corresponding JP Patent Application No. 2019-201667, dated Feb. 20, 2024, along with an English translation thereof.
Extended European Search Report Issued in Corresponding EP Patent Application No. 20883729.4, dated Nov. 3, 2023.
International Search Report issued in International Patent Application No. PCT/JP2020/041020, dated Dec. 15, 2020, along with an English translation thereof.
Office Action issued in Corresponding JP Patent Application No. 2019-201667, dated Oct. 17, 2023, along with an English translation thereof.
Office Action issued in Corresponding CN Patent Application No. 202080076216.X, dated Feb. 25, 2025, along with an English translation thereof.

* cited by examiner

F I G .  1
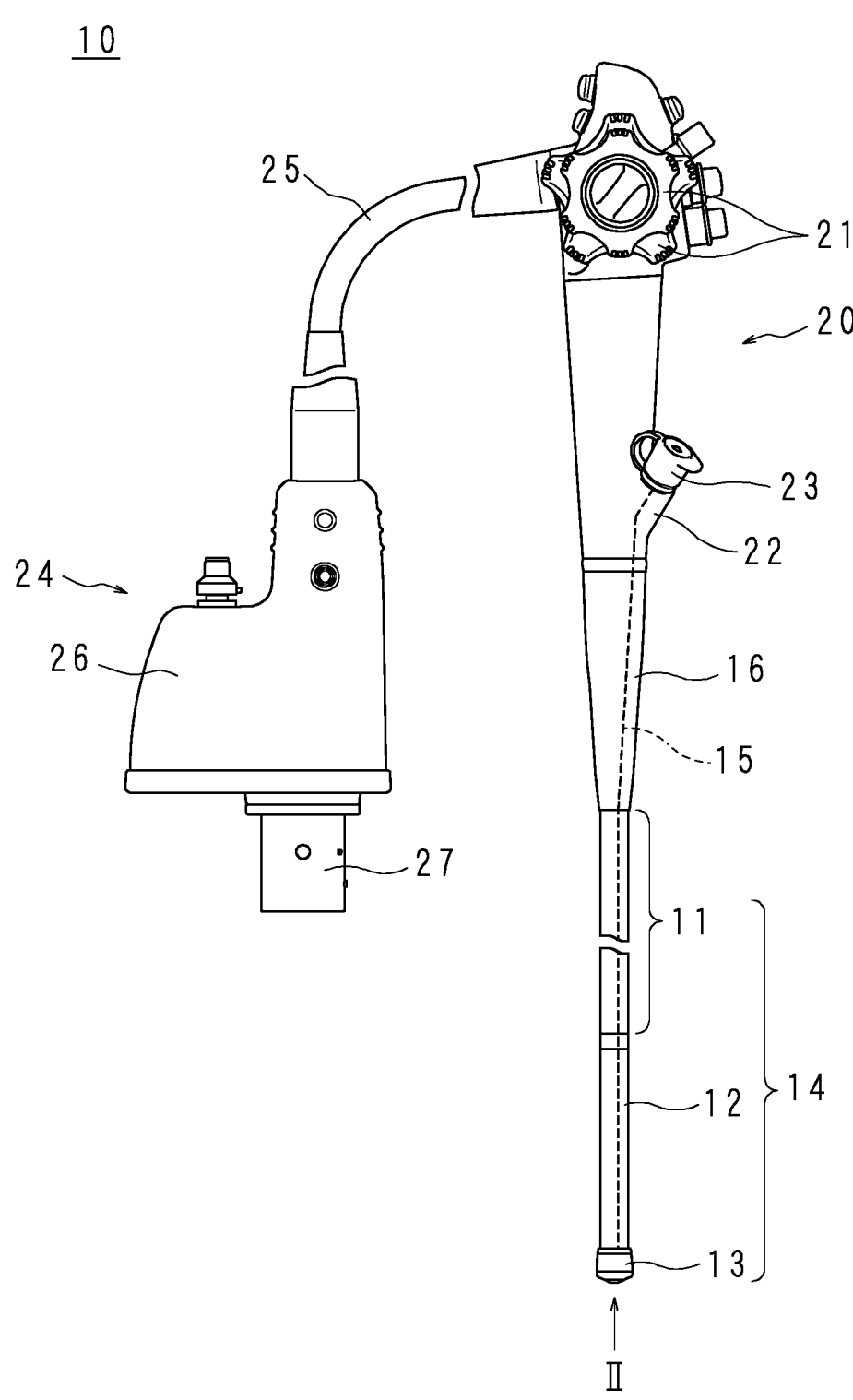

F I G. 2
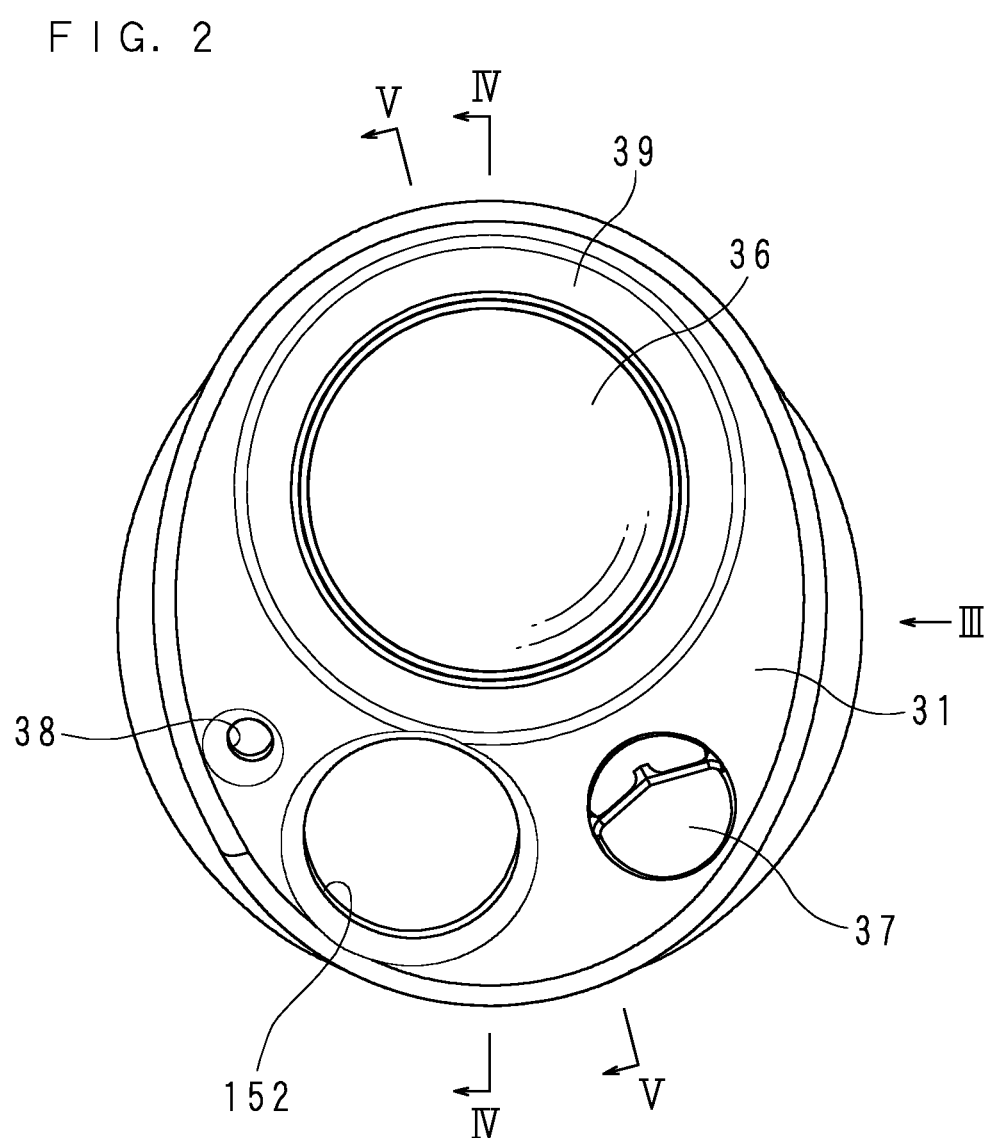

F I G. 3
<u>10</u>
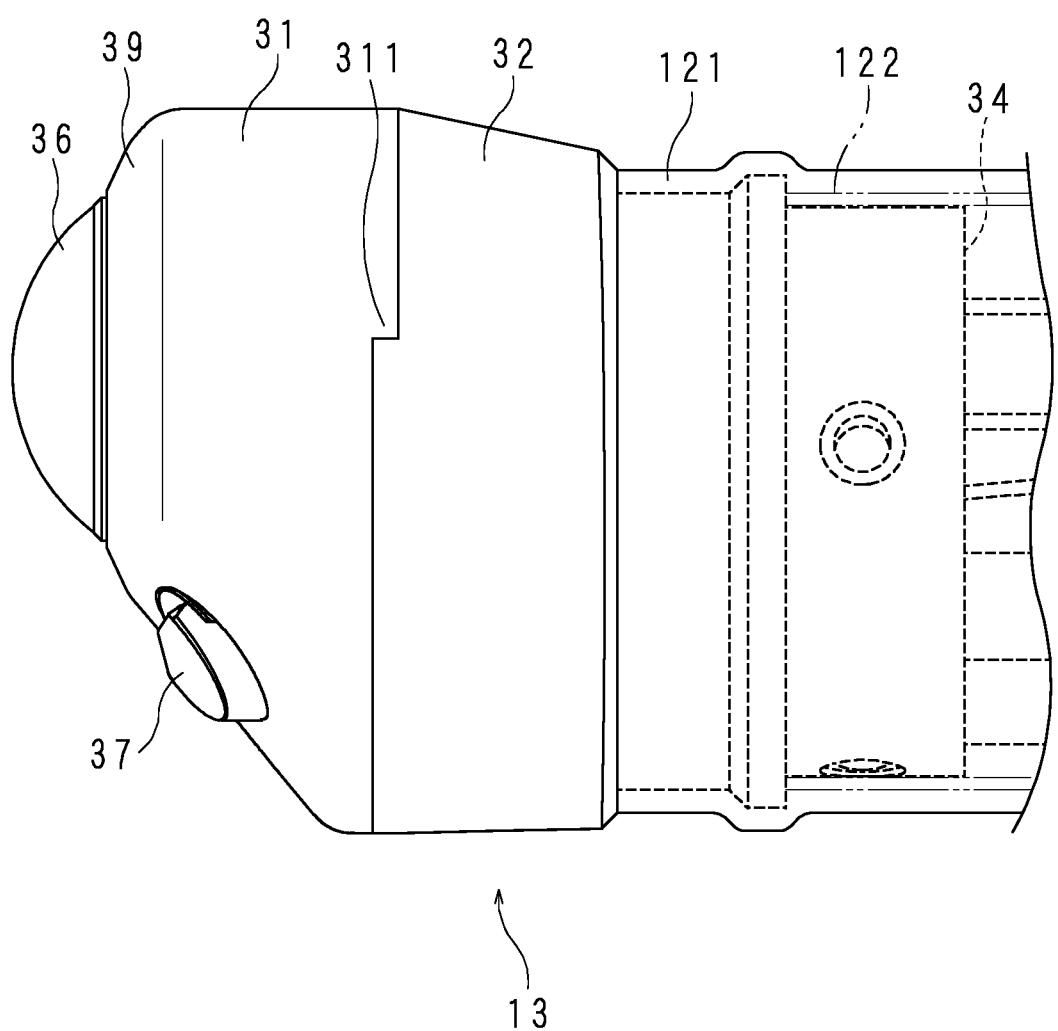

F I G. 4
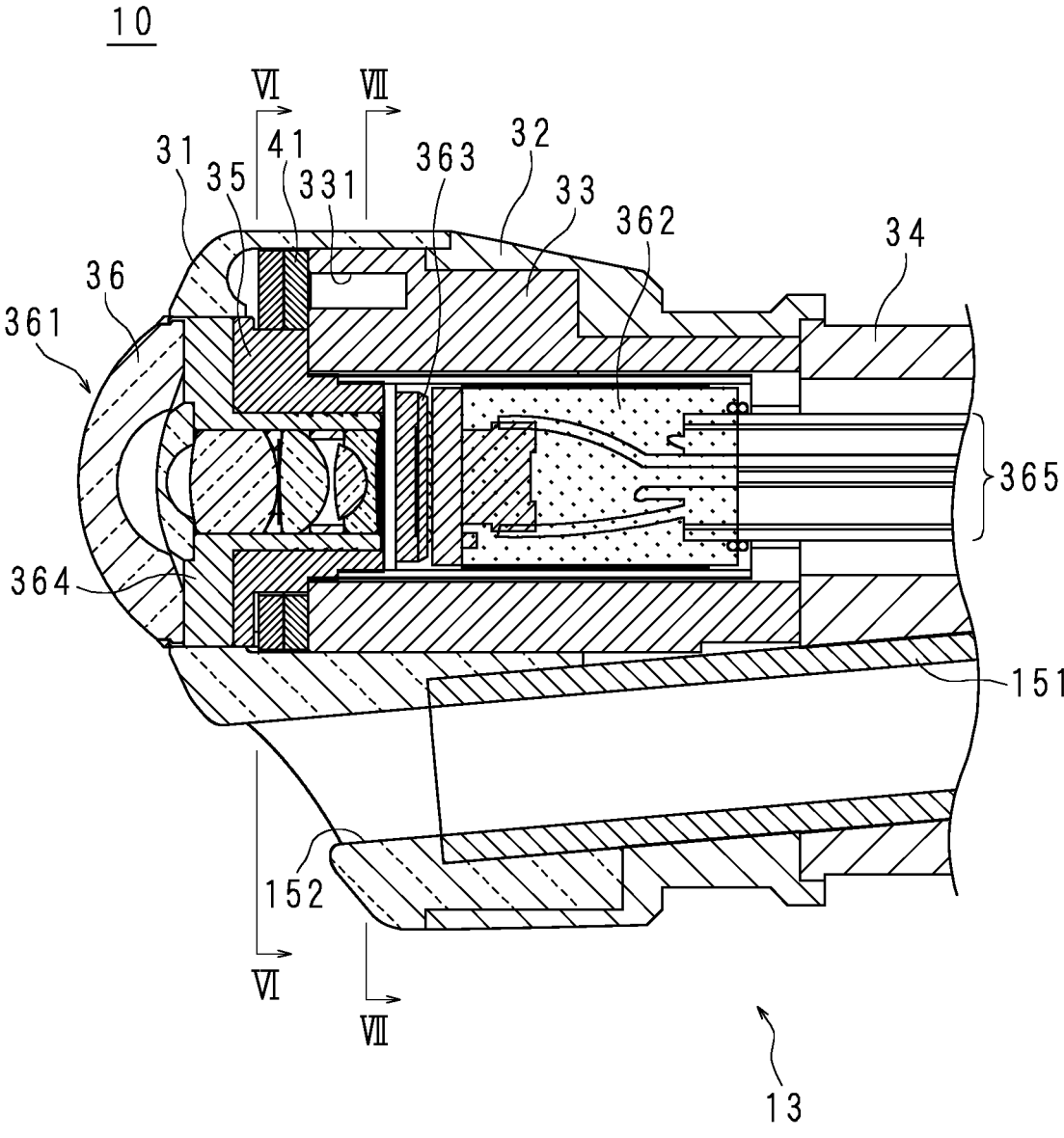

F I G. 6
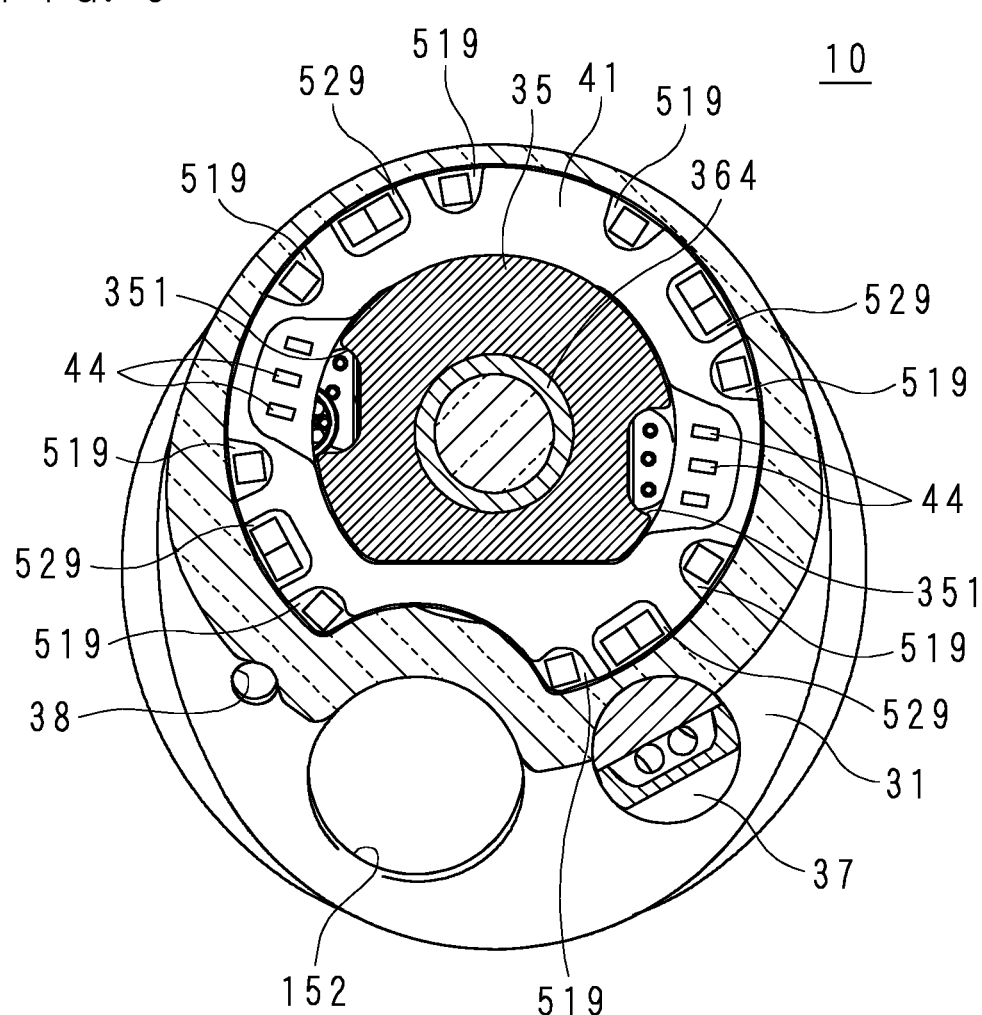

F I G. 7
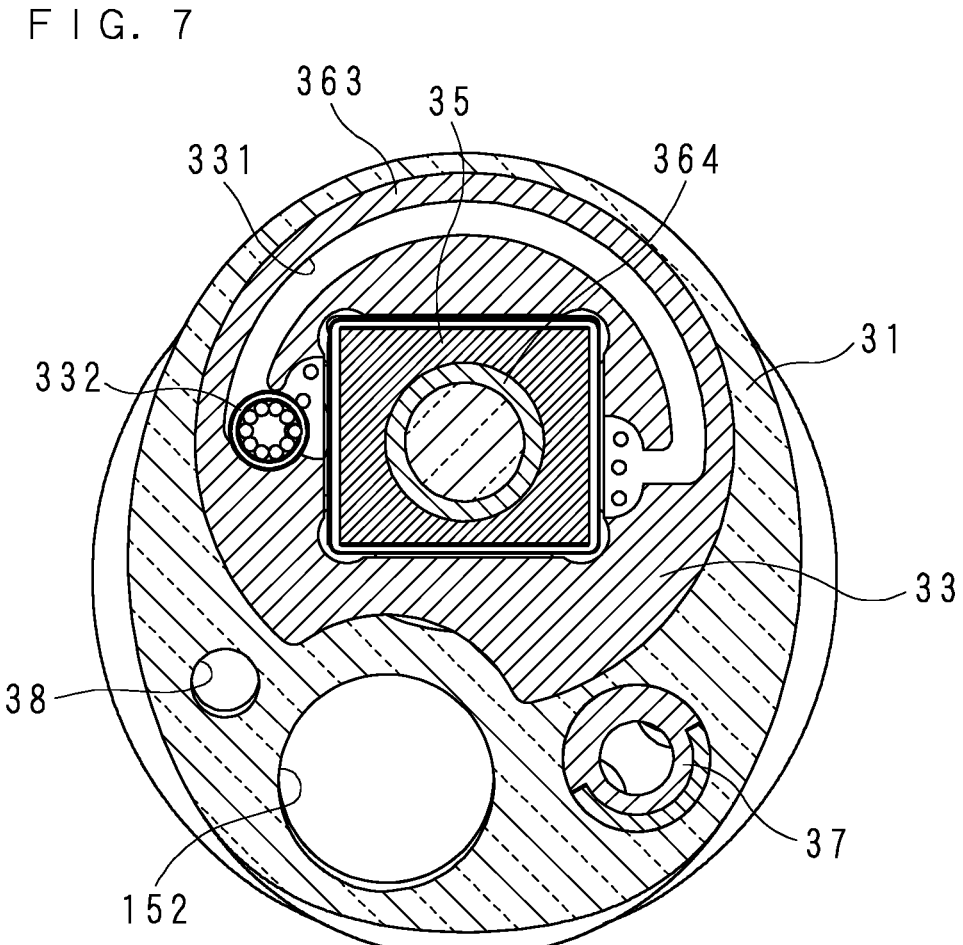

F I G.  8
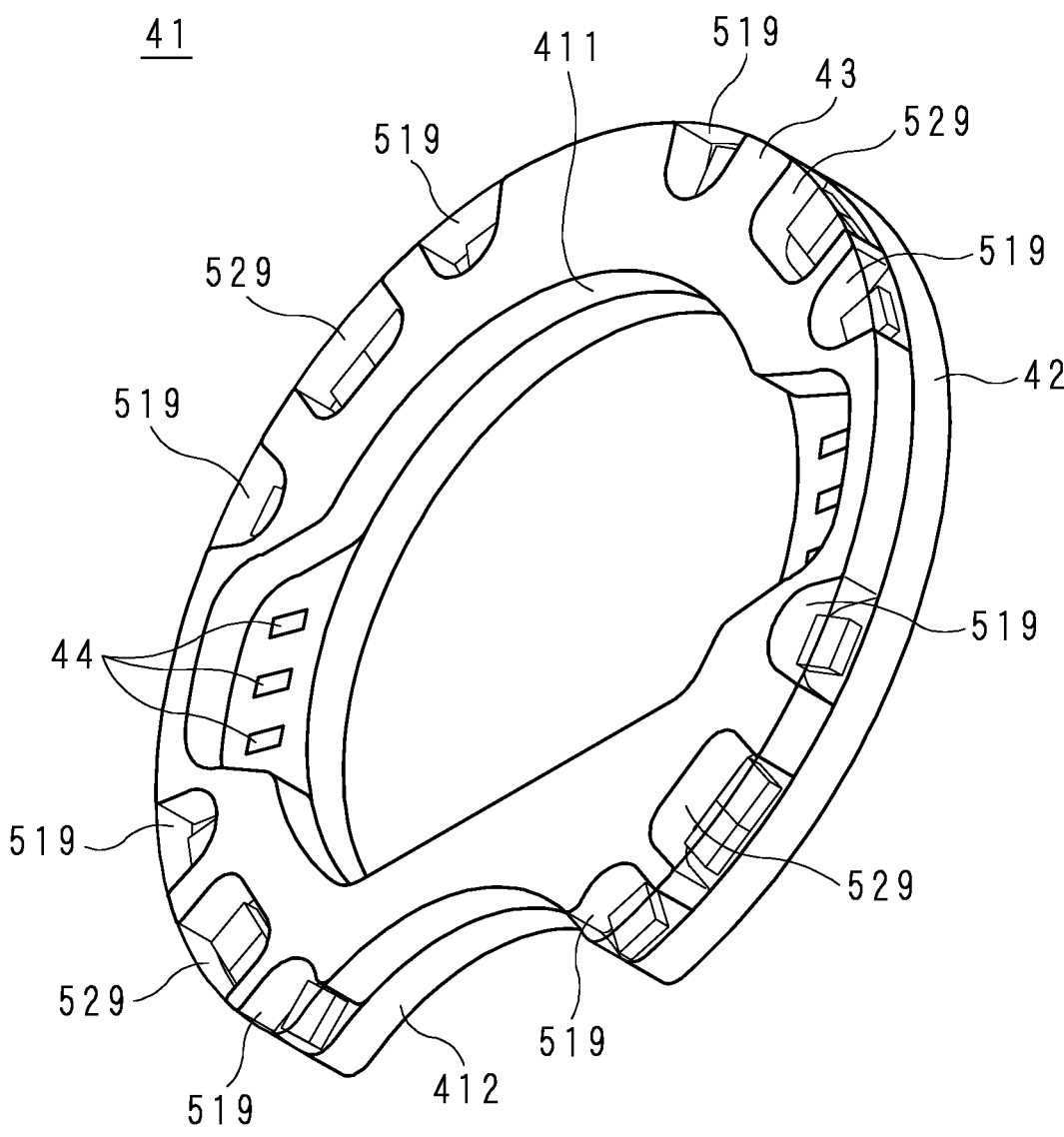

F I G. 9
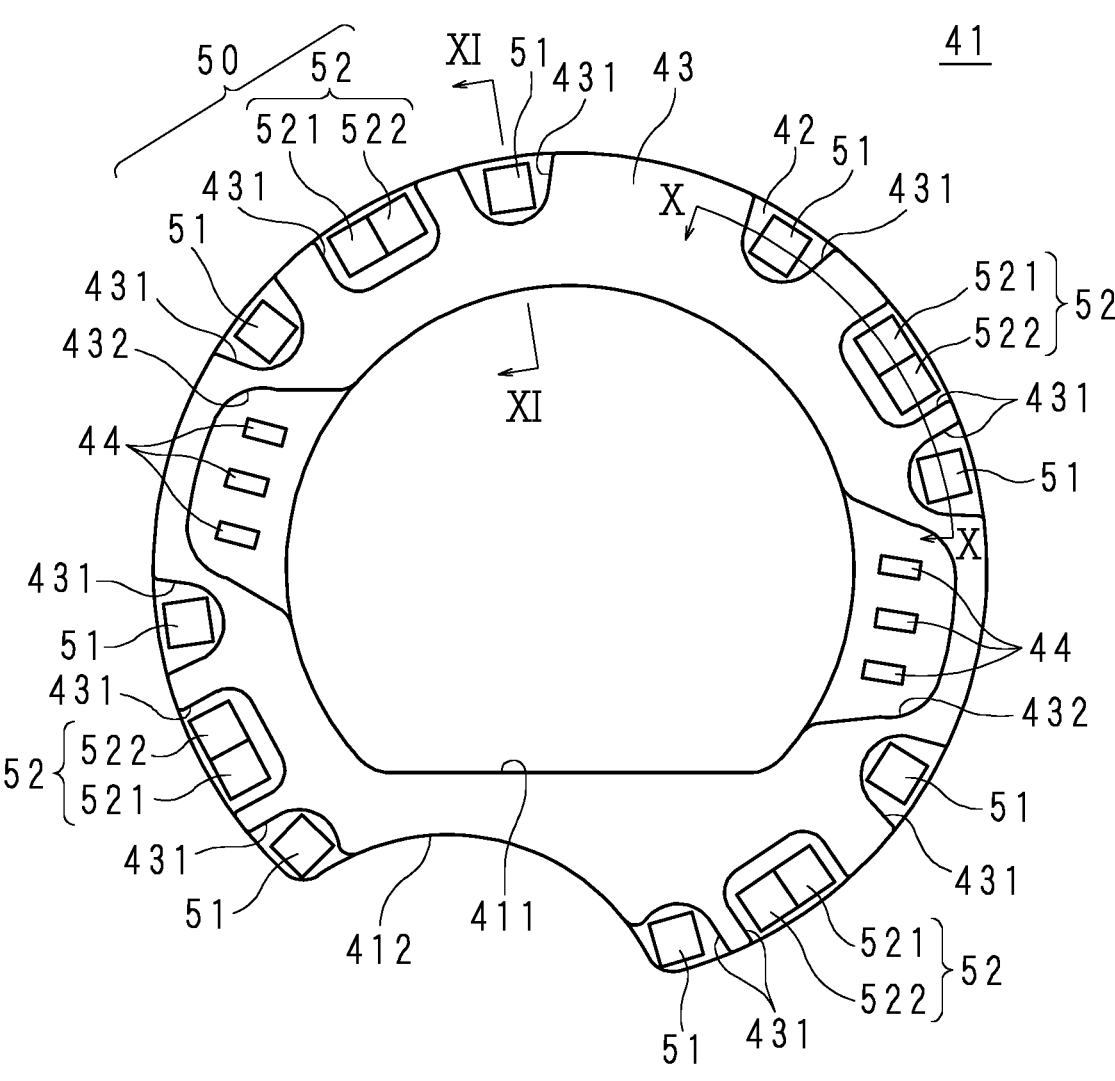

F I G. 1 0
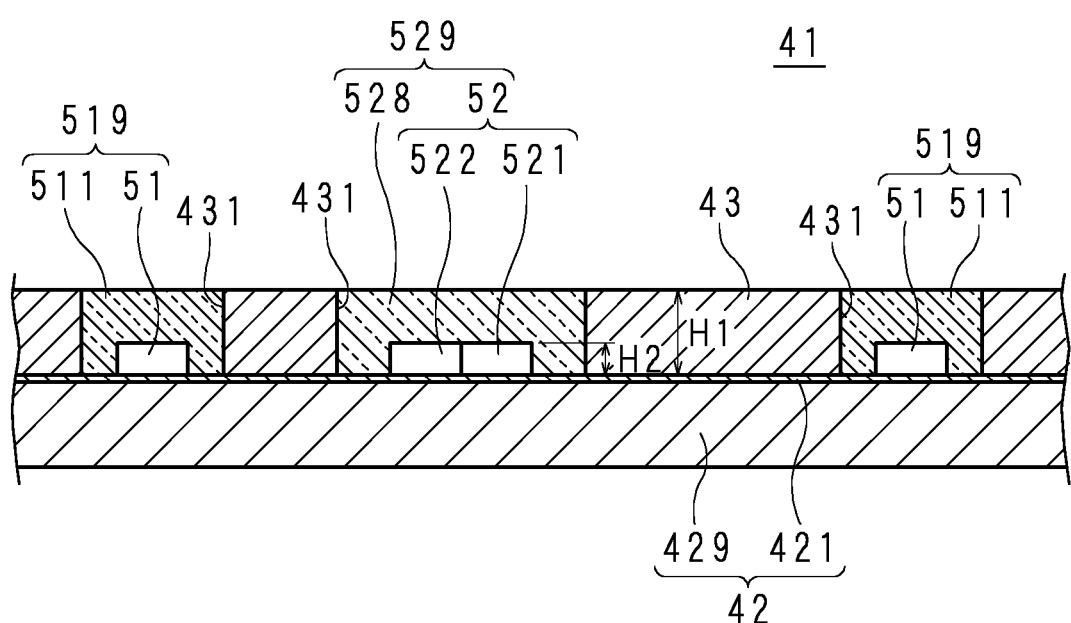

F I G. 1 1
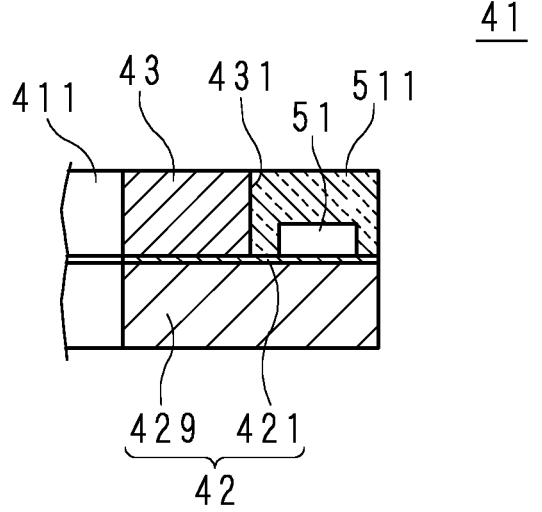

F I G. 1 2
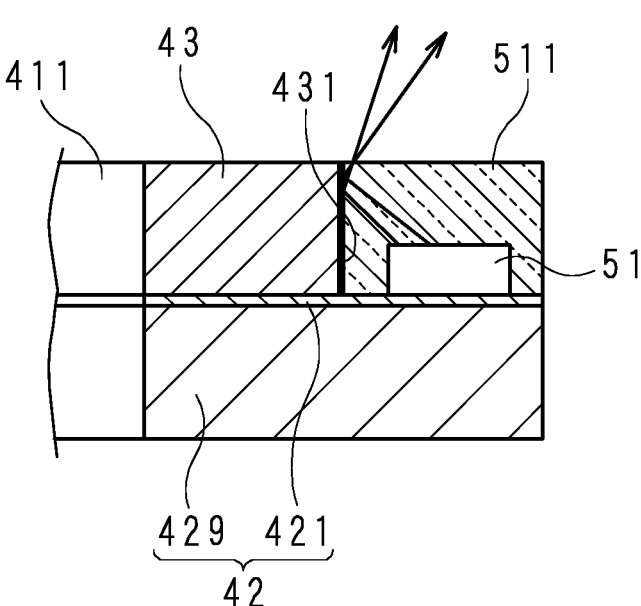

F I G.  1 3
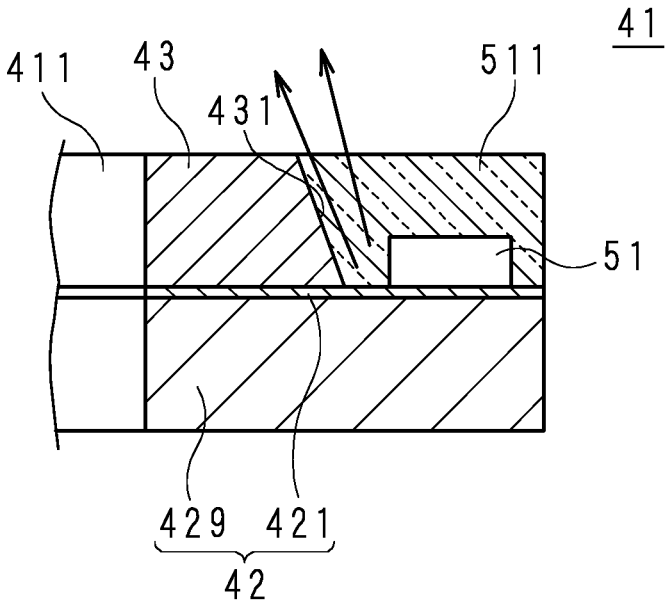

FIG. 14

ENDOSCOPE AND ENDOSCOPE ILLUMINATION SUBSTRATE

CROSS-REFERENCE TO RELATED APPLICATIONS

This application is the national phase under 35 U.S.C. § 371 of PCT International Application No. PCT/JP2020/041020 which has an International filing date of Nov. 2, 2020, which claims priority under 35 U.S.C. § 119 on Patent Application No. 2019-201667 filed in Japan on Nov. 6, 2019, and designated the United States of America.

FIELD OF THE INVENTION

The present invention relates to an endoscope and an endoscope illumination substrate.

BACKGROUND OF THE INVENTION

In Japanese Patent Application Laid-Open Publication No. 2005-74034, an endoscope disposed with alternating white light emitting parts and narrow band light emitting parts circumferentially has been disclosed. The white light emitting parts are used for illumination upon a normal light observation. The narrow band light emitting parts are used for illumination upon a special light observation.

SUMMARY OF THE INVENTION

A white light emitting parts is achieved by, for example, a combination of a blue light emitting element and a fluorescent substance that is excited by blue light to emit yellow light. In the case where light emitted from the narrow band light emitting part is applied to the fluorescent substance at the white light emitting part, a so-called cross talk occurs in which the white light emitting part emits light when it is to be in a non-light emitting state. The light emission by crosstalk affects the color tone of an endoscopic image.

In one aspect, an object is to provide an endoscope and the like that prevents crosstalk between multiple light emitting parts.

An endoscope comprises: an observation window that is disposed at a distal end of an insertion part; a plurality of first light-emitting parts that are disposed around the observation window; a second light-emitting part that is disposed between the first light-emitting parts and emits light at a bandwidth different from a bandwidth of light emitted by the first light-emitting parts; and a light-shielding body that is disposed between one of the first light-emitting parts and the second light-emitting part.

In one aspect, it is possible to provide an endoscope or the like that prevents crosstalk between multiple light emitting parts.

The above and further objects and features will more fully be apparent from the following detailed description with accompanying drawings.

BRIEF DESCRIPTION OF THE DRAWINGS

FIG. 1 is an outer appearance of an endoscope.
FIG. 2 is a drawing when viewed from the arrow direction II in FIG. 1.
FIG. 3 is a drawing when viewed from the arrow direction III in FIG. 2.

FIG. 4 is a partially sectional view of the endoscope taken along the line IV-IV in FIG. 2.
FIG. 6 is a partially sectional view of the endoscope taken along the line VI-VI in FIG. 4.
FIG. 7 is a partially sectional view of the endoscope taken along the line VII-VII in FIG. 4.
FIG. 8 is a perspective view of an endoscope illumination substrate.
FIG. 9 is a front view of the endoscope illumination substrate.
FIG. 10 is a partially sectional view of the endoscope illumination substrate taken along the line X-X in FIG. 9.
FIG. 11 is a partially sectional view of the endoscope illumination substrate taken along the line XI-XI in FIG. 9.
FIG. 12 is a partially sectional view of an endoscope illumination substrate according to Embodiment 2.
FIG. 13 is a partially sectional view of an endoscope illumination substrate according to Embodiment 3.
FIG. 14 is a partially sectional view of an endoscope illumination substrate according to Embodiment 4.

DETAILED DESCRIPTION

Embodiment 1

Figure 5:
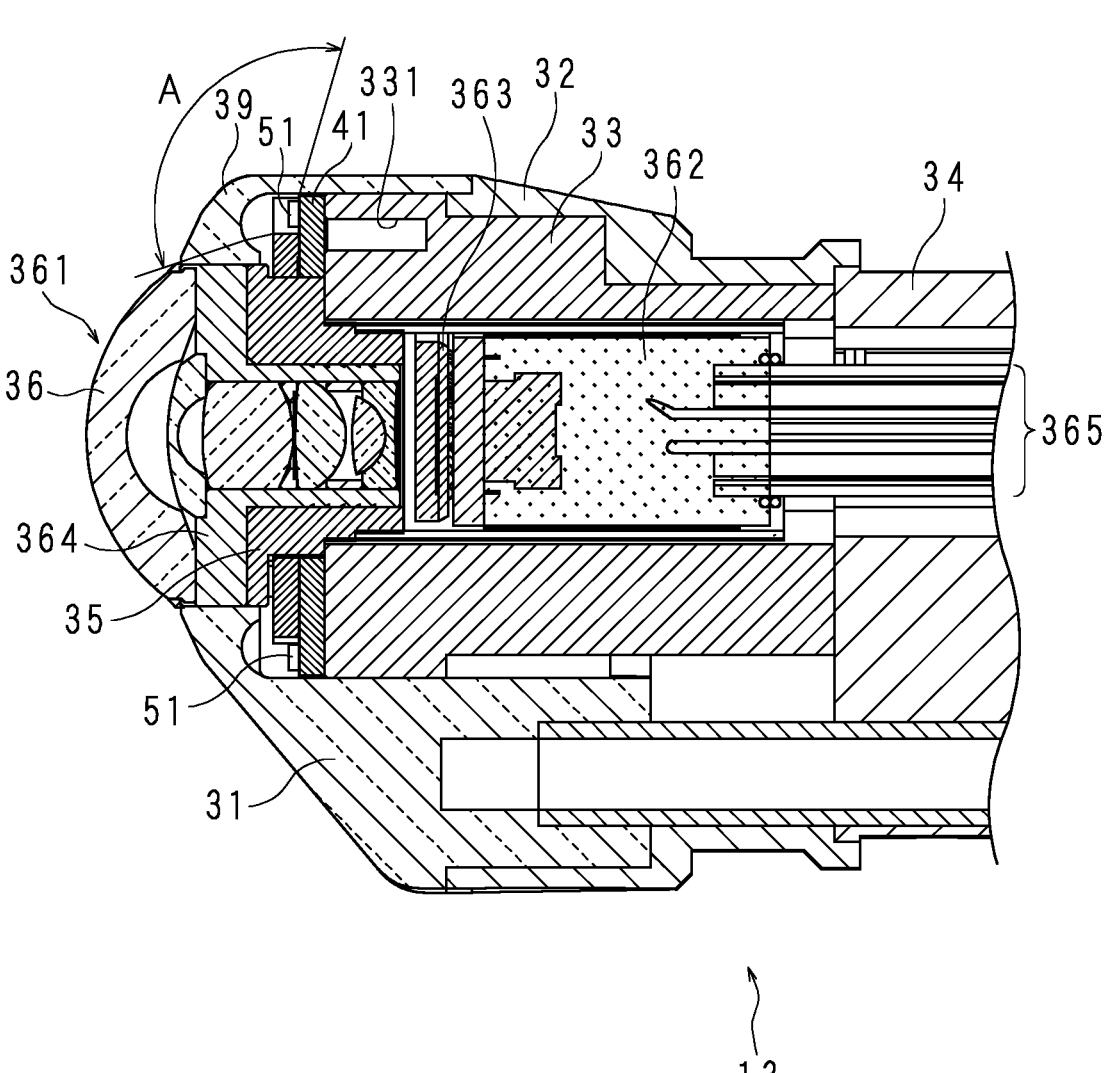
FIG. 5 is a partially sectional view of the endoscope taken along the line V-V in FIG. 2.

FIG. 1 illustrates the outer appearance of an endoscope 10. An endoscope 10 according to the present embodiment is a flexible endoscope for a gastrointestinal tract. The endoscope 10 has an insertion part 14, an operation part 20, a universal cord 25 and a connector part 24. The operation part 20 has a bend control knob 21 and a channel inlet 22.

The insertion part 14 is long and has an end connected to the operation part 20 via a bending proof portion 16. The insertion part 14 has, from the operation part 20 side, a flexible section 11, a bending section 12 and a distal end section 13. The bending section 12 bends in response to the operation of the bend control knob 21.

Between the channel inlet 22 and the distal end section 13, a channel 15 running through the insertion part 14 is provided. The channel inlet 22 is attached with a forceps plug 23 through which a treatment tool or the like is inserted.

In the following description, the longitudinal direction of the insertion part 14 will be referred to as an insertion direction. Likewise, along the insertion direction, the side closer to the operation part 20 will be referred to as an operation part side, whereas the side farther from the operation part 20 will be referred to as a distal end side.

The universal cord 25 is long, and has a first end connected to the operation part 20 and a second end connected to the connector part 24. The connector part 24 is covered with a connector case 26 having a shape of a substantially rectangular parallelepiped. A scope connector 27 protrudes from one of the surfaces of the connector case 26. The connector part 24 is connected to an endoscope processor or the like (not illustrated).

FIG. 2 is a drawing when viewed from the arrow direction II in FIG. 1. FIG. 3 is a drawing when viewed from the arrow direction III in FIG. 2. FIG. 2 shows a state in which the end face of the insertion part 14 is viewed from the front. FIG. 3 illustrates a side surface of the distal end section 13.

As illustrated in FIG. 2, an observation window 36 is disposed at a position shifted upward from the central axis of the insertion part 14 in FIG. 2. As illustrated in FIG. 3, the observation window 36 is dome-shaped. An annular illumination window 39 is disposed in such a manner as to surround the observation window 36. The details of the illumination window 39 will be described later.

At the bottom right from the observation window 36 in FIG. 2, an air/water supply nozzle 37 is disposed with an outgoing outlet facing the observation window 36. At the bottom left from the observation window 36, a channel outlet 152 and a distal end water delivery hole 38 are disposed.

Note that FIG. 2 is one example of the appearance of the end face of the distal end section 13, and the arrangement of the respective parts is not limited to FIG. 2. For example, an air supply nozzle and a water supply nozzle may separately be provided in place of the air/water supply nozzle 37.

As illustrated in FIG. 3, the distal end section 13 has a first frame 31 and a second frame 32 from the distal end side. The lower half of the first frame 31 in FIG. 3, that is, the part where the air/water supply nozzle 37, a channel outlet 152 and the distal end water delivery hole 38 are provided, has a substantially conical surface.

The first frame 31 has a projection portion 311 projecting toward the operation part side at the upper part in FIG. 3. The part corresponding to the projection portion 311 at the edge of the second frame 32 on the distal end side is retracted toward the operation part side. The projection portion 311 is engaged with the recess of the second frame 32 to restrict the rotation angle between the first frame 31 and the second frame 32.

The operation part side of the second frame 32 is secured with a fourth frame 34. A bending piece 122 shown by a dot-dot-dash line in FIG. 3 is fit into the fourth frame 34 and secured there. The operation part side of the second frame 32 and the bending piece 122 are covered with a bend rubber 121.

FIG. 4 is a partially sectional view of the endoscope 10 taken along the line IV-IV in FIG. 2. FIG. 5 is a partially sectional view of the endoscope 10 taken along the line V-V in FIG. 2. FIG. 6 is a partially sectional view of the endoscope 10 taken along the line VI-VI in FIG. 4. FIG. 7 is a partially sectional view of the endoscope 10 taken along the line VII-VII in FIG. 4. In FIG. 4 and FIG. 5, the bending piece 122 and the bend rubber 121 are not illustrated.

The above-described first frame 31, second frame 32 and fourth frame 34 are tubular. Inside the first frame 31 and the second frame 32, a tubular third frame 33 is contained. The third frame 33 is a stepped drum being thick on the distal end side while being narrow on the operation part side. As illustrated in FIG. 7, the third frame 33 has a circular cross section on the outer side and a rectangular cross section on the inner side. The dimension of the rectangular at the inner peripheral edge is substantially equal through the entire length of the third flame 33.

At the end face on the distal end side of the third frame 33, an annular endoscope illumination substrate 41 is disposed. At the peripheral edge of the surface on the distal end side of the endoscope illumination substrate 41, first light-emitting elements 51 and second light-emitting elements 52 (see FIG. 9) that emit illumination light are mounted. The details of the configuration of the endoscope illumination substrate 41 will be described later. Note that if there is no need to distinguish the first light-emitting element 51 from the second light-emitting element 52, they are simply described as a light-emitting element 50 (see FIG. 9).

The first frame 31 is made of a translucent resin permeable to light emitted from the light-emitting element 50. As illustrated in FIG. 5, a part of the inner surface of the first frame 31 facing the light-emitting element 50 is recessed in a U-shaped groove to form a concave lens. The advantages of the concave lens and a side surface of the light-emitting element 50 not being covered with a light-shielding body 43 allow light emitted from the light-emitting element 50 to illuminate a wide area ranging from the front to the sides as illustrated by a reference code A in FIG. 5.

The part of the first frame 31 permeable to light emitted from the light-emitting element 50 serves as an illumination window 39. The distal edge of the first frame 31 may be made of a translucent resin while the other part thereof may be made of a non-translucent resin. The distal edge of the first frame 31 may be made of any translucent material such as a translucent resin, a translucent ceramic or the like while the other part thereof may be made of any material such as a resin, metal, a ceramic or the like.

A tabular fifth frame 35 is inserted to the endoscope illumination substrate 41 and the third frame 33. The outer peripheral edge of the cross section of the fifth frame 35 on the distal side is substantially D-shaped with the straight line portion of the D shape facing the channel outlet 152 side as illustrated in FIG. 6 while the outer peripheral edge of the cross section of the fifth frame 35 on the operation side is rectangular as illustrated in FIG. 7. The hole that penetrates the fifth frame 35 in the longitudinal direction has a circular cross section with a uniform thickness.

As illustrated in FIG. 6, two cable grooves 351 extending in the longitudinal direction of the fifth frame 35 are provided at the curved portion of the substantially D shape of the fifth frame 35. The two cable grooves 351 are arranged substantially symmetrically. A bottom portion of the cable grooves 351 is substantially flush with the side surface of the short side of the rectangular cross-section as illustrated with reference to FIG. 7.

Returning to FIGS. 4 and 5, a lens unit 361 is inserted to the fifth frame 35 from the distal end side. The lens unit 361 has a lens frame 364 and multiple lenses secured in the lens frame 364. The periphery of the lens located closest to the distal end side out of the lenses consisting of the lens unit 361 is disposed to merge smoothly with the periphery of the recess of the first frame 31. The above-described observation window 36 corresponds to the outer surface of the lens arranged closest to the distal end side.

The lens unit 361 according to the present embodiment is a so-called super-wide angle lens with a viewing angle of 150 degrees or over. The lens unit 361 includes a lens with a large diameter on the distal end side and a lens with small diameter on the operation part side. The lens frame 364 has a cylindrical shape with a flange on the distal end side. The lens with a large diameter located at the distal end side is secured to the flange part of the lens frame 364 while the lens with a small diameter located at the operation part side is secured to the internal surface of the lens frame 364.

At the operation part side of the lens unit 361, an imaging unit 362 is disposed. The imaging unit 362 is a member including an imaging element 363 arranged at the end face on the distal end side, a driver circuit and a cable connected thereto that are solidified in a substantially rectangular parallelepiped shape. The imaging unit 362 includes an imaging cable 365 extending toward the operation part side. The imaging cable 365 is a bundle of multiple cables. The imaging cable 365 is connected to the endoscope processor via the operation part 20, the universal cord 25 and the connector part 24.

The positional relation between the lens unit 361 and the imaging unit 362 is adjusted so that light incident on the lens unit 361 forms an image on the imaging element 363. The lens unit 361 and the imaging unit 362 form an observation optical system of the endoscope 10.

The first frame 31 is provided with through holes respectively corresponding to the channel outlet 152, the air/water supply nozzle 37 and the distal end water delivery hole 38. As illustrated in FIG. 4, the through hole corresponding to the channel outlet 152 is a stepped hole having a large inside diameter on the operation part side and is connected to a channel tube 151.

Though not illustrated, the through hole corresponding to the distal end water delivery hole 38 is connected to a distal end water delivery tube. The through hole corresponding to the air/water supply nozzle 37 is attached with the air/water supply nozzle 37 on the distal end side while being attached with an air supply tube and a water supply tube on the operation part side.

FIG. 8 is a perspective view of the endoscope illumination substrate 41. FIG. 9 is a front view of the endoscope illumination substrate 41.

As described above, the endoscope illumination substrate 41 is annular. The endoscope illumination substrate 41 has a substantially D-shaped imaging hole 411 at its center portion. The outer periphery near the straight line portion of the imaging hole 411 of the endoscope illumination substrate 41, a substantially arcuate channel concave portion 412 is provided.

The endoscope illumination substrate 41 has a laminated structure of a base substrate 42 and a light-shielding body 43. The base substrate 42 is mounted with eight first light-emitting elements 51 and four second light-emitting elements 52. The 20 second light-emitting elements 52 each include a green light-emitting element 521 and a purple light-emitting element 522 adjacently arranged along the outer periphery of the endoscope illumination substrate 41.

The first light-emitting elements 51 are dispersedly arranged at substantially equally spaced intervals along the circumference of the base substrate 42. At the above-described channel concave portion 412 is disposed so as to be positioned between the two adjacent first light-emitting elements 51.

The second light-emitting element 52 is arranged between the two adjacent first light-emitting elements 51 at every other space. The second light-emitting elements 52 are also dispersedly arranged at substantially equally spaced intervals along the circumference of the base substrate 42.

The first light-emitting elements 51 and the second light-emitting elements 52 are spaced at a substantially equal distance from an optical axis of an observation optical system composed of the imaging unit 362 and the lens unit 361.

Two groups of three wire lands 44 are respectively arranged at spaces having no second light-emitting element 52 interposed between the first light-emitting elements 51. The two groups of the wire lands 44 are disposed to face each other across the central portion of the base substrate 42. The wire lands 44 are one example of a cable connection part according to the present embodiment.

The light-shielding body 43 is stacked on the base substrate 42 except for the locations where the light-emitting elements 50 are mounted and their surrounding areas and the locations where the wire lands 44 are arranged and their surrounding areas. In the vicinity of the location where the first light-emitting element 51 is mounted, the end face of the light-shielding body 43 surrounds the first light-emitting element 51 to form a U-shaped light-shielding face 431 that opens toward the outer periphery of the endoscope illumination substrate 41.

In the vicinity of the place where the second light-emitting element 52 is mounted as well, the end face of the light-shielding body 43 surrounds the green light-emitting element 521 and the purple light-emitting element 522 to form a U-shaped light-shielding face 431 that opens toward the outer periphery of the endoscope illumination substrate 41.

In the vicinity of the location where the wire lands 44 are arranged, the end face of the light-shielding body 43 surrounds the three wire lands 44 to form a U-shaped connection part wall surface 432 that opens toward the inner periphery of the endoscope illumination substrate 41.

As illustrated in FIG. 5, the endoscope illumination substrate 41 is assembled in the endoscope 10 with the mounting surface on which the light-emitting elements 50 are mounted facing toward the distal end side.

FIG. 10 is a partially sectional view of the endoscope illumination substrate 41 taken along the line X-X in FIG. 9. FIG. 11 is a partially sectional view of the endoscope illumination substrate 41 taken along the line XI-XI in FIG. 9. FIG. 10 illustrates a cross section of the endoscope illumination substrate 41 taken along an arcuate curved line substantially parallel with the outer periphery of the endoscope illumination substrate 41, including two first light-emitting elements 51 and a second light-emitting element 52 that is interposed between them. FIG. 11 illustrates a cross section of the endoscope illumination substrate 41 taken along a face passing through a single first light-emitting element 51 and extending in the radial direction. In FIG. 10 and FIG. 11, the illustration of the internal structure of the light-emitting element 50 and the wiring pattern provided on the endoscope illumination substrate 41 are not made.

The surrounding area of the first light-emitting element 51 is filled with a fluorescent resin 511. The details of the fluorescent resin 511 will be described later. The surrounding area of the second light-emitting element 52 is filled with a translucent resin 528. The fluorescent resin 511 and the translucent resin 528 fill the space surrounded by the U-shaped light-shielding face 431, the base substrate 42, the outer peripheral surface of the endoscope illumination substrate 41 and the main surface of the endoscope illumination substrate 41 on the light-shielding body 43 side. The endoscope illumination substrate 41 is formed in a plate with uniform thickness except for the surrounding areas of the wire lands 44 by the filled resins.

The base substrate 42 is in the form of laminations of a wiring board 421 and a support plate 429. The wiring board 421 is a so-called printed circuit board (PCB) having a laminated structure of an insulating layer and a wiring layer. The wiring board 421 may be a so-called hard substrate employing a hard material such as a glass epoxy substrate or the like for the insulating layer, or may be a so-called a flexible printed circuit (FPC) employing a polyimide sheet or the like for the insulating layer.

Though not illustrated, the base substrate 42 is a so-called multilayer circuit board, and formed with wiring for connecting the lands where the light-emitting elements 50 are mounted and the wire lands 44.

The support plate 429 is a plate for supporting the wiring board 421 and preventing a breaking wire due to bending or the like of the wiring board 421. The support plate 429 is a metal plate made of, for example, copper, aluminum, stainless steel or the like. The support plate 429 may be a ceramic plate or a resin plate. In the case where the support plate 429 is conductive, an insulating layer formed with no pattern is disposed on a side of the wiring board 421 that is in contact with the support plate 429.

The light-shielding body 43 is a metal plate, for example, a copper plate, an aluminum plate or the like. The light-shielding body 43 may be a plate made of a ceramic or a resin having a light blocking effect. In the case where the light-shielding body 43 is conductive, an insulating layer formed with no pattern is disposed at a location of the wiring board 42 that is in contact with the light-shielding body 43. The desirable thickness of the light-shielding body 43 will be described later.

The support plate 429 and the wiring board 421 as well as the wiring board 42 and the light-shielding body 43 are fixed by any method such as adherence, chemical bonding or the like.

Returning to FIG. 7, an illumination cable 332 extends from the endoscope processor to the distal end section 13 via the connector part 24, the universal cord 25 and the operation part 20. The illumination cable 332 is a bundle of multiple cables. In FIG. 7, the illumination cable 332 is disposed at the left from the fifth frame 35.

The illumination cable 332 is separated into two bundles at the distal end section 13. One of the bundles is drawn out to the vicinity of the left side wire land 44 after passing through the left side cable groove 351 in FIG. 6. The other one of the bundles is drawn out to the vicinity of the right side wire land 44 after routed through a substantially U-shaped wire groove 331 provided in the third frame 33 and then passing through the right side cable groove 351 in FIG. 6.

Each cable strand of the illumination cable 332 are connected to the wire lands 44 by any method such as soldering or the like. It is noted that the cable strands connected to the respective wire lands 44 are not illustrated in FIG. 6. The light illumination of the light-emitting element 50 is controlled by the endoscope processor through the illumination cable 332.

The fluorescent resin 511 will be described. In the present embodiment, the first light-emitting element 51 is a so-called light source for normal light observation while the second light-emitting element 52 is a so-called light source for special light observation. For the normal light observation, white light with a wide bandwidth is employed. However, a semiconductor light-emitting element such as light emitting diode (LED), for example, is a narrow band light emitting element for emitting narrow band light with a narrow band width.

A technique of obtaining white light has been developed by hitting narrow band light emitted from a semiconductor light-emitting element with a fluorescent substance to emit a mixed light of fluorescence radiated from the fluorescent substance and the light radiated from the semiconductor light-emitting element. For example, it has already been known that white light is obtained according to the combinations shown in Table 1.

TABLE 1

| No. | Color of Light-Emitting Element | Color of Fluorescent Substance |
|---|---|---|
| 1 | blue | yellow |
| 2 | near ultraviolet light | red + green + blue |

In the present embodiment, a case where the combination of No. 1 is employed for the first light-emitting element 51 will be described as an example. Namely, the fluorescent resin 511 according to the present embodiment is a resin obtained by mixing a translucent resin and a yellow fluorescent substance, and the first light-emitting element 51 is a blue LED. The first light-emitting element 51 and the fluorescent resin 511 constitute a first light-emitting part 519 according to the present embodiment.

It is noted that any combination capable of obtaining illumination light suitable for the normal light observation as well as the combination of No. 2 in Table 1 may be employed for the color of the light-emitting element and the color of the fluorescent substance.

A so-called white light-emitting element, which contains a semiconductor light-emitting element and a fluorescent substance sealed in a package, may be employed for the first light-emitting element 51. In the case where the white light-emitting element is employed, there is no need to cover the first light-emitting element 51 with the fluorescent resin 511. The thickness of the white light-emitting element may be substantially the same as that of the light-shielding body 43. The white light-emitting element may be covered with a transparent resin not containing a fluorescent substance as in the second light-emitting element 52.

Illumination light for special light observation emitted from the second light-emitting element 52 will be described. The special light observation is a technique for highlighting a blood vessel running through the deep region below a mucous membrane by using narrow-band illumination light. A method of utilizing the illumination light shown in Table 2 is proposed, for example.

TABLE 2

| No. | Color of Light-Emitting Element |
|---|---|
| 1 | combination of blue + green |
| 2 | purple |
| 3 | combination of green + purple |
| 4 | combination of blue + green + red |

It is desirable that the colors shown in Table 2 are each narrow band light with a narrow bandwidth. A semiconductor light-emitting element such as an LED, a semiconductor laser or the like may be employed for the second light-emitting element 52. In the present embodiment, a case where employment of the combination of No. 3 will be described as an example, in which the green light-emitting element 521 and the purple light-emitting element 522 are used.

It is noted that filling the surrounding areas of the green light-emitting element 521 and the purple light-emitting element 522 with the translucent resin 528 prevents reduction in reliability due to water entering the endoscope illumination substrate 41, for example. The green light-emitting element 521 and the purple light-emitting element 522 constitute a second light-emitting part 529 according to the present embodiment. The second light emitting part 529 does not necessarily include the translucent resin 528.

Returning to FIG. 10, the function of the light-shielding body 43 will be described. In the case where the normal light observation is performed, the first light-emitting element 51 is turned on while the second light-emitting element 52 is turned off. The light emitted from the first light-emitting element 51 is turned to white light by the action of the fluorescent substance in the fluorescent resin 511 to illuminate the front and sides through the illumination window 39.

In the case where the special light observation is performed, the first light-emitting element 51 is turned off while the second light-emitting element 52 is turned on. The light emitted from the second light-emitting element 52 illuminates the front and sides through the illumination window 39.

Assuming that the light emitted from the second light-emitting element 52 is incident on the fluorescent resin 511, crosstalk occurs in which the fluorescent resin 511 emits light. In other words, though the special light observation is being performed, the first light-emitting part 519 becomes a pseudo light-emitting state.

The presence of the light-shielding body 43 can prevent or reduce crosstalk in which light emitted from the second light-emitting element 52 enters the fluorescent resin 511, which thereby emits light.

With reference to the surface of the base substrate 42, the height H1 of the light-shielding body 43 is higher than the height H2 of the second light-emitting element 52. The height H1 of the light-shielding body 43 is desirably at least two times greater than the height H2 of the second light-emitting element 52. With reference to the surface of the base substrate 42, the height H1 of the light-shielding body 43 is desirably at least two and a half times greater than the height H2 of the second light-emitting element 52.

According to the present embodiment, the endoscope 10 that prevents crosstalk between multiple light-emitting parts can be provided. Since the white illumination light for the normal observation does not cause crosstalk due to the illumination light for the special light observation, image quality upon the special light observation is improved.

According to the present embodiment, since light emitted from the side surface of the light-emitting elements 50 disposed near the observation window 36 is not shut off, the endoscope 10 that illuminates even the sides of the insertion part 14 can be provided. Since the illumination light reaches up to the end of the observation visual field using the observation optical system with a wide angle, the endoscope 10 that is capable of observing a wide visual field can be provided.

It is noted that the light-shielding face 431 may be formed on a surface of high reflectivity by grinding or the like. The endoscope 10 that is capable of illuminating the sides of the insertion part 14 can be provided.

A material having high thermal conductivity such as metal or the like is employed for the support plate 429 and the light-shielding body 43, whereby the endoscope 10 that is capable of promptly diffusing heat occurring in the light-emitting element 50 can be provided. The thermal diffusion is promptly performed within the endoscope illumination substrate 41, and thus by disposing a heat dissipation sheet or a cooling element at any place of the endoscope illumination substrate 41, the endoscope illumination substrate 41 can be protected from heat.

Since the first light-emitting elements 51 and the second light-emitting elements 52 are evenly arranged, the endoscope 10 that causes less variations in luminance can be provided. Since the green light-emitting elements 521 and the purple light-emitting elements 522 are respectively arranged adjacent to each other, the endoscope 10 that causes less color irregularities of illumination light for the special light observation can be provided.

By provision of the U-shaped concave lens formed in the internal surface of the first frame 31, light emitted from the light-emitting element 50 is diffused. Thus, the endoscope 10 that is capable of illuminating the wide range can be provided.

It is noted that the shapes of the lenses formed in the internal surface of the first frame 31 may be different between the part facing the first light-emitting element 51 and the part facing the second light-emitting element 52. For example, the lenses formed in the internal surface of the first frame 31 are formed such that light emitted from the first light-emitting element 51 is diffused in a wide range while light emitted from the second light-emitting element 52 is strongly emitted to the area ahead of the insertion part 14.

In the case where the endoscope 10 with wide observation angle is used as in the present embodiment, illumination light for normal light observation needs to also illuminate the sides of the insertion part 14. The user can find the part of a lesion while observing a wide range at the same time.

If conducting the special light observation during the endoscopy, the user operates the endoscope 10 such that the target region is positioned at the central portion of the visual field of the endoscope. Accordingly, it is desirable that the illumination light for the special light observation emitted from the second light-emitting element 52 mainly illuminates the central portion of the visual field. The central portion of the visual field can be brightly illuminated since the illumination light is not diffused to the periphery portion of the visual field.

The light emitted from the first light-emitting element 51 is diffused in a wide range while the light emitted from the second light-emitting element 52 is strongly emitted toward the area ahead of the insertion part 14. This makes it possible to provide the endoscope 10 that illuminates ranges suitable for the normal light observation and the special light observation.

The channel concave portion 412 is provided at the outer periphery of the endoscope illumination substrate 41, so that the observation window 36 and the channel outlet 152 can be disposed close to each other. This makes it possible to provide the endoscope 10 having the distal end section 13 with a thinner diameter.

Embodiment 2

The present embodiment relates to an endoscope 10 in which the light-shielding face 431 is a reflecting surface for reflecting light. Components common to those of Embodiment 1 are not described.

FIG. 12 is a partially sectional view of an endoscope illumination substrate 41 according to Embodiment 2. FIG. 12 illustrates a cross section as in FIG. 11. Though not illustrated, the light-shielding face 431 surrounding the second light-emitting element 52 also has a shape similar to that of the light-shielding face 431 surrounding the first light-emitting element 51.

In the present embodiment, a reflecting surface shown by a bold line is formed on the surface of the light-shielding face 431. The reflecting surface is a surface smoothed by grinding the light-shielding face 431, for example. The reflecting surface may be formed by a reflecting film such as a nickel chrome plating film or the like formed on the surface of the light-shielding face 431.

As illustrated by the arrows in FIG. 12, light emitted from the first light-emitting element 51 and the fluorescent resin 511 impinges on and is reflected by the light-shielding face 431, and the reflected light is emitted to the area ahead of the insertion part 14. That is, the light emitted from the light-emitting element 50 can be utilized with efficiency.

According to the present embodiment, the endoscope 10 having high utilization efficiency of light reflected from the light-emitting element 50 can be provided.

Embodiment 3

The present embodiment relates to the endoscope 10 in which the light-shielding face 431 is partially formed in an inclined surface. Components common to those of Embodiment 1 are not described.

FIG. 13 is a partially sectional view of an endoscope illumination substrate 41 according to Embodiment 3. FIG. 13 is a cross section as in FIG. 11. In the present embodiment, a part closer to the center of the endoscope illumination substrate 41 of the light-shielding face 431 is so inclined that the distance from the center of the endoscope illumination substrate 41 is shorter as it is more separated from the base substrate 42.

In the present embodiment, the cross section of the endoscope illumination substrate 41 taken along an arcuate curved line substantially parallel with the outer periphery of the endoscope illumination substrate 41 is as in FIG. 10. In other words, the part of the light-shielding face 431 that is vertical to the circumferential direction is formed in a vertical surface. Though not illustrated, the light-shielding face 431 surrounding the second light-emitting element 52 also has a similar shape as the light-shielding face 431 surrounding the first light-emitting element 51.

As illustrated by the arrows in FIG. 13, the light emitted from the first light-emitting element 51 and the fluorescent resin 511 to the center of the insertion part 14 can be radiated without being shut off by the light-shielding body 43.

According to the present embodiment, the endoscope 10 having high utilization efficiency of light reflected from the light-emitting element 50 can be provided.

Embodiment 4

The present embodiment relates to the endoscope 10 in which the light-shielding face 431 is entirely formed in an inclined surface. Components common to those of Embodiment 2 are not described.

Figure 14:
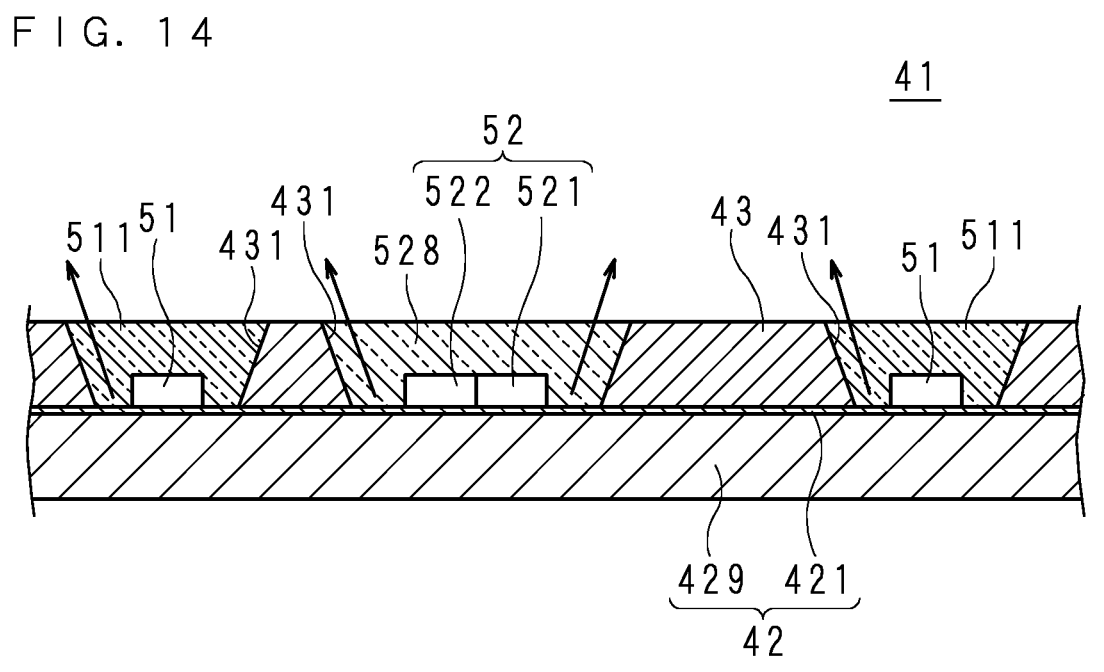

FIG. 14 is a partially sectional view of an endoscope illumination substrate 41 according to Embodiment 4. FIG. 14 shows the cross section of the endoscope illumination substrate 41 taken along an arcuate curved line substantially parallel with the outer periphery of the endoscope illumination substrate 41 as in FIG. 10. The cross section in the radial direction of the endoscope illumination substrate 41 is as in FIG. 13.

In the present embodiment, the light-shielding face 431 is entirely formed in an inclined surface that becomes wider as it is far away from the base substrate 42. Though not illustrated, the light-shielding face 431 surrounding the second light-emitting element 52 also has a shape similar to the light-shielding face 431 surrounding the first light-emitting element 51.

As illustrated by the arrows in FIGS. 13 and 14, light obliquely emitted from the first light-emitting element 51 and the fluorescent resin 511 is radiated without being shut off by the light-shielding body 43.

According to the present embodiment, the endoscope 10 having high utilization efficiency of light reflected from the light-emitting element 50 can be provided.

Embodiment 5

The present embodiment relates to the endoscope 10 in which a part of the wiring board 421 is formed thicker. Components common to those of Embodiment 2 are not described.

Figure 15:
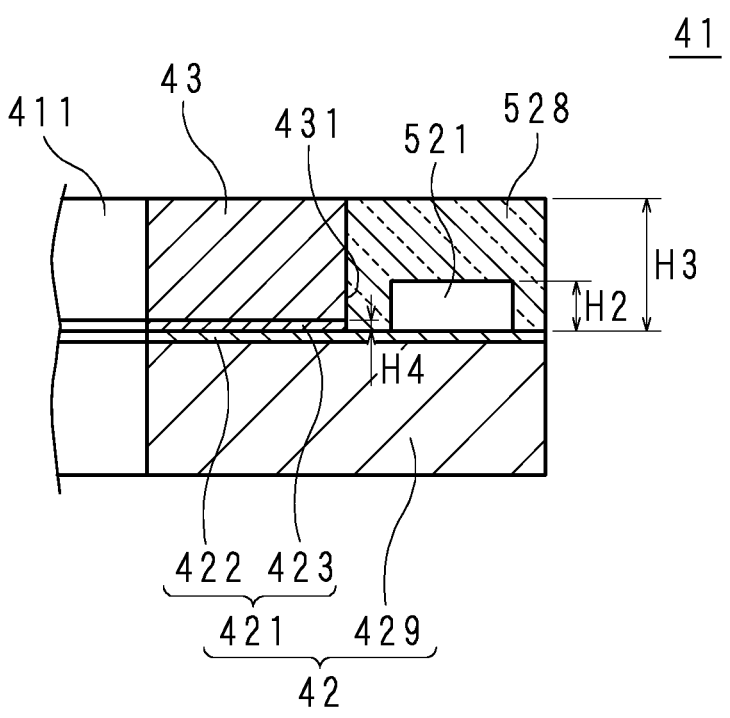
FIG. 15 is a partially sectional view of an endoscope illumination substrate according to Embodiment 5.

FIG. 15 is a partially sectional view of an endoscope illumination substrate 41 according to Embodiment 5. FIG. 15 is a cross section of the endoscope illumination substrate 41 taken along a face passing through a single green light-emitting element 521 and extending in the radial direction.

The wiring board 421 according to the present embodiment includes a first substrate layer 422 and a second substrate layer 423. The first substrate layer 422 and the second substrate layer 423 are stacked with each other to form a single piece. The land mounted with the light-emitting element 50 such as the green light-emitting element 521 or the like is provided on the first substrate layer 422. The end face of the second substrate layer 423 is flush with the light-shielding face 431.

The wire lands 44 may be provided on the first substrate layer 422 or on the second substrate layer 423.

With reference to the surface mounted with the light-emitting element 50, i.e., the surface of the first substrate layer 422, the height H3 of the light-shielding body 43 is higher than the height H2 of the second light-emitting element 52. The height H3 of the light-shielding body 43 is desirably two times greater than the height H2 of the second light-emitting element 52. With reference to the surface mounted with the light-emitting element 50, the height H3 of the light-shielding body 43 is more desirably two and half times greater than the height H2 of the second light-emitting element 52.

In the case where an insulating layer forming of the second substrate layer 423 has translucency, it is desirable that the height H4 of the second substrate layer 423 is equal to or less than the height H2 of the second light-emitting element 52. This prevents crosstalk that causes the fluorescent resin 511 to emit light by the light transmitted through the insulating layer while being reflected by the wiring pattern provided inside the insulating layer.

According to the present embodiment, the thick wiring board 421 can be utilized while the total thickness of the endoscope illumination substrate 41 is the same as that in Embodiment 1. Since the wiring board 421 is thinner at the location where the second light-emitting element 52 is mounted, a crosstalk prevention effect as in Embodiment 1 or the like can be produced.

Since a wiring pattern can be routed at the second substrate layer 423, a necessary wiring pattern can be provided without increasing the outside diameter of the endoscope illumination substrate 41 even if the wiring between the wire lands 44 and the light-emitting element 50 is complicated.

Any of the technical features (the constituent features) described in the respective embodiments can be combined with each other, and such a combination can form a new technical feature. It should be considered that the embodiments disclosed this time are illustrative in all aspects and are not limitative. The scope of the present invention is indicated not by the meaning described above but by the claims, and all changes that fall within the meaning equivalent to the claims and the scope are to be embraced.

It is to be noted that, as used herein and in the appended claims, the singular forms "a", "an", and "the" include plural referents unless the context clearly dictates otherwise.

10 endoscope
   11 flexible section
   12 bending section
   121 bend rubber
   122 bending piece
   13 distal end section
   14 insertion part
   15 channel
   151 channel tube
   152 channel outlet
   16 bending proof portion
   20 operation part 21 bending knob
22 channel inlet
23 forceps plug
24 connector part
25 universal cord
26 connector case
27 scope connector
31 first frame
311 projection portion
32 second frame
33 third frame
331 wire groove
332 illumination cable
34 fourth frame
35 fifth frame
351 cable groove
36 observation window
361 lens unit
362 imaging unit
363 imaging element
364 lens frame
365 imaging cable
37 air/water supply nozzle
38 distal end water delivery hole
39 illumination window
41 endoscope illumination substrate
411 imaging hole
412 channel concave portion
42 base substrate
421 wiring board
422 first substrate layer
423 second substrate layer
429 support plate
43 light-shielding body
431 light-shielding face
432 connection portion wall surface
44 wire land
50 light-emitting element
51 first light-emitting element
511 fluorescent resin
519 first light-emitting part
52 second light-emitting element
521 green light-emitting element
522 purple light-emitting element
528 translucent resin
529 second light-emitting part

The invention claimed is:

1. An endoscope comprising:
an observation window that is disposed at a distal end of an insertion part;
an endoscope illumination substrate having an annular shape;
a plurality of first light-emitters that are disposed around the observation window;
a second light-emitter that is disposed between at least two of the plurality of the first light-emitters and emits light at a bandwidth different from a bandwidth of light emitted by the plurality of first light-emitters; and
a light-shielding body that is disposed between at least one of the plurality of first light-emitters and the second light-emitter,
wherein the plurality of first light-emitters and the second light-emitter are provided along an outer periphery of the endoscope illumination substrate, wherein the endoscope illumination substrate includes:
a base substrate having a mounting surface mounted with light-emitting elements respectively included in the plurality of first light-emitters and the second light-emitter, and
the light-shielding body stacked on a part of the base substrate on which the light-emitting elements are not mounted,
wherein the light-shielding body has a light-shielding face that surrounds each of the light-emitting elements in a U-shape that opens to an outer periphery of the insertion part in at least an extension direction of the insertion part, and
wherein the endoscope illumination substrate is configured to entirely surround the observation window when viewed in a direction orthogonal to the extension direction of the insertion part.

2. The endoscope according to claim 1, wherein
each of the plurality of first light-emitters includes a white light-emitting element, and
the second light-emitter includes a narrow band light-emitting element.

3. The endoscope according to claim 1, wherein
each of the plurality of first light-emitters includes:
a light-emitting element, and
a fluorescent substance-containing resin that covers the light-emitting element.

4. The endoscope according to claim 1, wherein the second light-emitter includes a purple light-emitting element or a green light-emitting element.

5. The endoscope according to claim 1, wherein the second light-emitter includes a blue light-emitting element or a green light-emitting element.

6. The endoscope according to claim 1, wherein the light-shielding body is made of copper or aluminum.

7. The endoscope according to claim 1, wherein each of the plurality of first light-emitters and the second light-emitter are spaced at an equal distance from an optical axis of the observation window.

8. The endoscope according to claim 1, wherein the light-shielding face is an inclined surface, such that a distance between the light-shielding face and the light-emitting element increases as a distance between the light-shielding face and the base substrate also increases.

9. The endoscope according to claim 1, wherein the base substrate includes:
a wiring board having the mounting surface, and
a support plate stacked on a reverse side of the mounting surface of the wiring board.

10. The endoscope according to claim 1, wherein
the base substrate is provided with a cable connection part on the mounting surface that is disposed along a periphery of a hole that surrounds the observation window, and
the light-shielding body has a connection part wall surface that surrounds the cable connection part in a U shape that opens to an inner periphery of the endoscope illumination substrate.

11. The endoscope according to claim 1, wherein the endoscope illumination substrate has an arcuate concave portion at an outer periphery part.

12. An endoscope illumination substrate, comprising:
a base substrate having a mounting surface;
a plurality of first light-emitters on the mounting surface;
a second light-emitter that is disposed between at least two of the plurality of first light-emitters and emits light at a bandwidth different from a bandwidth of light emitted by the plurality of first light-emitters; and a light-shielding body that is disposed between at least one of the plurality of first light-emitters and the second light-emitter, wherein the plurality of first light-emitters and the second light-emitter are provided along an outer periphery of the annular base substrate of the endoscope illumination substrate, wherein the endoscope illumination substrate includes:

the base substrate having a mounting surface mounted with light-emitting elements respectively included in the plurality of first light-emitters and the second light-emitter, and the light-shielding body stacked on a part of the base substrate on which the light-emitting elements are not mounted, wherein the light-shielding body has a light-shielding face that surrounds each of the light-emitting elements in a U-shape that opens to an outer periphery of the insertion part in at least an extension direction of the insertion part, and wherein the endoscope illumination substrate is configured to entirely surround an observation window when viewed in a direction orthogonal to the extension direction of the insertion part.

13. The endoscope illumination substrate according to claim 12, wherein each of the plurality of first light-emitters includes a white light-emitting element, and the second light-emitter includes a narrow band light emitting element.

14. The endoscope illumination substrate according to claim 12, wherein each of the plurality of first light-emitters includes:

a light-emitting element, and a fluorescent substance-containing resin that covers the light-emitting element.

* * * * *